United States Patent
Hsieh

(10) Patent No.: US 10,342,974 B2
(45) Date of Patent: Jul. 9, 2019

(54) METHOD FOR INTERFERENTIAL CURRENT STIMULATION BY COMPLEX ACTIVE REGIONS

(71) Applicant: Kou-Chang Hsieh, Taipei (TW)

(72) Inventor: Kou-Chang Hsieh, Taipei (TW)

(*) Notice: Subject to any disclaimer, the term of this patent is extended or adjusted under 35 U.S.C. 154(b) by 413 days.

(21) Appl. No.: 15/392,179

(22) Filed: Dec. 28, 2016

(65) Prior Publication Data

US 2017/0182315 A1 Jun. 29, 2017

(30) Foreign Application Priority Data

Dec. 28, 2015 (TW) .............................. 104144111 A

(51) Int. Cl.
*A61N 1/04* (2006.01)
*A61N 1/32* (2006.01)
*A61N 1/36* (2006.01)
*A61N 1/06* (2006.01)

(52) U.S. Cl.
CPC ......... *A61N 1/323* (2013.01); *A61N 1/36014* (2013.01); *A61N 1/36034* (2017.08); *A61N 1/0484* (2013.01); *A61N 1/06* (2013.01); *A61N 1/36003* (2013.01)

(58) Field of Classification Search
CPC ........................... A61N 1/323; A61N 1/36034
USPC ........................................................ 607/48
See application file for complete search history.

*Primary Examiner* — Nadia A Mahmood
(74) *Attorney, Agent, or Firm* — C. G. Mersereau; DeWitt LLP

(57) ABSTRACT

A method for interferential current stimulation by complex active regions, in which the method is adapted to generate low frequency interference active regions formed of staggered electric flux lines by disposing electrodes to stimulate specific parts of a human body by supplying electricity is provided. The method includes following steps: providing a power supply section configured to supply power having two different frequencies including a first frequency power source and corresponding electrical wires thereof and a second frequency power source and corresponding electrical wires thereof; and providing an electrode disposing section configured to provide plural electrodes respectively connected to the first frequency power source and the second frequency power source via the corresponding electrical wires, and interfere each other for generating plural low frequency active regions provided for stimulating a specific part of the human body to achieve the effect of curing various symptoms and muscle trainings.

16 Claims, 17 Drawing Sheets

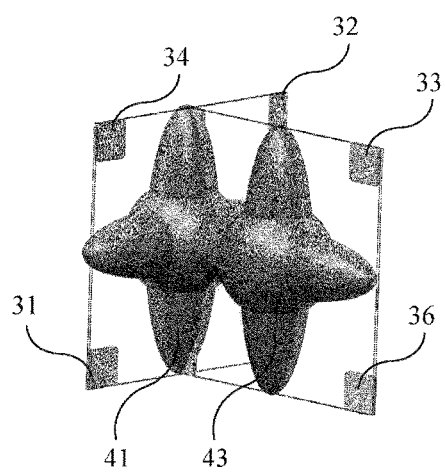 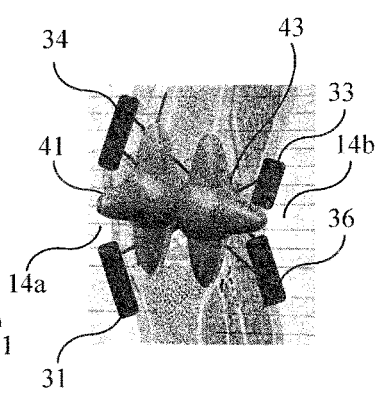
FIG. 3A      FIG. 3B      FIG. 3C

METHOD FOR INTERFERENTIAL CURRENT STIMULATION BY COMPLEX ACTIVE REGIONS

CROSS-REFERENCE TO RELATED APPLICATION

This application claims the priority benefit of Taiwanese Patent Application No. 104144111, filed on Dec. 28, 2015. The entirety of the above-mentioned patent application is hereby incorporated by reference herein and made a part of this specification.

BACKGROUND OF THE INVENTION

Field of the Invention

The invention relates to a method for interferential current stimulation by complex active regions, and particularly relates to a method for interferential current stimulation by complex active regions adapted to generate a plurality of low frequency interference active regions formed of a plurality of staggered electric flux lines by disposing a plurality of electrodes so as to stimulate a plurality of specific parts of a human body by supplying electricity.

Background

In recent years, with a lot of innovative progresses in human body clinical experiments for electrical stimulating physical therapies, in addition to therapies originally acting on muscles, nerves and muscle trainings with interferential current stimulations, physical therapies with interferential current stimulations can also activate the lymph, circulating the blood, boosting metabolisms and improving detoxifications. In addition, by stimulating the nerve tissue in the human body with currents, it is able to generate endorphins and serotonins or even adjust nerves. At the end of the 20th century and 2the first century as today, such technology has gradually applied to various diseases caused by pelvic cavity dysfunctions and symptoms including such as excretory disorders, urinary incontinences, sexual dysfunctions, muscle looseness after prostate surgery and uterus muscles looseness after giving birth, etc. Interferential current stimulations can even provide excellent therapies to other fields such as some physical muscle trainings like core muscles strengthening of human bodies and cyst fluid circulation of joints which preventing the degeneration of joints. Therefore, the physical therapy method with interferential current stimulations nowadays has been commonly applied to joints, abdomens, pelvic cavities, and body support core muscles in the pelvic cavity (including abdominis, lumbar, pelvic floor muscles). Moreover, the method of interferential current stimulation therapy of pelvic cavity and trainings of core muscles also demonstrates great significance in the treatment for different shapes of gastrointestinal, excretory, reproductive organs stack with each other in the abdomen and pelvis.

Nevertheless, these abdomens, pelvic cavities, even every joint of the human body are of certain depths in human bodies. General speaking, the interferential current stimulation therapy method uses a high frequency current within thousands to tens of thousands Hz in human bodies or the deep parts of joints with the characteristic of low resistance in human bodies; then the interfering method is used to generate a low-frequency interference inside the body in order to conduct an interferential current stimulation therapy. Due to the diversity of the applications of the interferential current stimulation therapy method, such method often requires different angles of stimulations for different organs such as pain killing points for knee joints are around the patella; the metabolism is at popliteus. As a result, the active angle of interferential current stimulations needs to be orthogonal with the inner patella to stimulate lymph and promote blood circulations in joints. Also, there are treatments for a single symptom that requires stimulating a plurality of organs with currents. For example, not only pelvic floor muscles but also pudendal nerves of coccyx area need to be strengthened with interferential current stimulations for urinary incontinences to improve frequency urinations and failing to control impulse urinations. However, currently, for the treatment of different parts of the same organ or a plurality of organs, the interferential current stimulation on only a specific portion for a single region is used.

In general, an interferential current stimulation treatment method uses a plurality of electrodes for attaching onto on appropriate positions of bodies in order to generate effects based on shapes and locations of organs to form a single active region and to achieve effective treatment of symptoms, which is also known as IFC (Interferential Current Stimulation). The basic operating theories and methods of IFC normally have an interferential current stimulation active frequency (under 200 Hz) for human bodies. But when a current frequency below 200 Hz is active in a human body, the electrical impedance in human body is over thousands of Ohm. The overly high electrical impedance causes most of the currents to be consumed in the skin layer without traveling deeper. However, the frequency that can penetrate into human bodies with thousands of Hz acting on human bodies but only requires an electrical impedance level below 100 Ohm. Although the use of such type of frequency allows penetration into bodies, overly high frequency of currents would not generate effects on human bodies. Therefore, two current frequencies of thousands Hz are utilized to generate interferences inside bodies in order to generate currents with a lower frequency in a specific portion or an organ such that the effect of interferential current stimulations can be achieved. For example: inside the active region 100 Hz (4100 Hz-4000 Hz) can generate (below 200 Hz) the effect of interferential current stimulations when two frequencies of 4000 Hz and 4100 Hz have an interference inside the body.

Such use of the characteristic of interferential current stimulation capable of penetrating into bodies deeply by adding a few pieces of electrodes in the interferential current stimulation system of a single interference active region with electrical wires is able to generate a plurality of active regions; in addition, according to the body parts which have electrodes attached thereto, combinations of various types of shapes and angles can be formed to apply a plurality of interferential current stimulations therapy on a single organ at different angles or for a plurality of organs.

SUMMARY OF THE INVENTION

The present invention provides a method for interferential current stimulation by complex active regions, which is adapted to generate a plurality of low frequency interference active regions formed of a plurality of staggered electric flux lines by disposing a plurality of electrodes so as to stimulate a plurality of specific parts of a human body by supplying electricity. The method for interferential current stimulation by complex active regions includes following steps: providing a power supply section configured to supply power having two different frequencies, in which the power supply section includes a first frequency power source, comprising the current between 1,000 Hz and 10,000 Hz and corresponding electrical wires; and a second frequency power source, comprising a physiological frequency source between the region of decreasing or increasing less than 200 Hz of first frequency power source and comprising corresponding electrical wires; and providing an electrode disposing section configured to provide a plurality of electrodes respectively connected to the first frequency power source and the second frequency power source via the corresponding electrical wires, wherein the electrode disposing section includes: a first electrode electrically connected to the first frequency power source via a corresponding electrical wire and disposed on a specific position; a second electrode electrically connected to the second frequency power source via a corresponding electrical wire and disposed on a specific position that forming a first electric flux line with the first electrode; a third electrode electrically connected to the first frequency power source via a corresponding electrical wire and disposed on a specific position that forming a second electric flux line with the second electrode; a fourth electrode electrically connected to the second frequency power source via a corresponding electrical wire and disposed on a specific position; a fifth electrode electrically connected to the second frequency power source via a corresponding electrical wire and disposed on a specific position that forming a third electric flux line with the fourth electrode; and a sixth electrode electrically connected to the second frequency power source via a corresponding electrical wire and disposed on a specific position that forming a fourth electric flux line with the fifth electrode, wherein the first and the third electric flux lines interfere each other for generating a first low frequency active region provided for stimulating a specific part of the human body; and wherein the second and the fourth electric flux lines interfere each other for generating a second low frequency active region provided for stimulating another specific part of the human body. The electrode disposing section further includes a seventh electrode electrically connected to the first frequency power source via a corresponding electrical wire and disposed on a specific position to form a fifth electric flux line with one of the second and the third electrodes; and an eighth electrode electrically connected to the second frequency power source via a corresponding electrical wire and disposed on a specific position to form a sixth electric flux line with one of the fifth and the sixth electrodes. The first and the third electric flux lines interfere each other to generate a first low frequency active region for stimulating a specific part of the human body. The second and the fourth electric flux line interfere each other to generate a second low frequency active region for stimulating a specific part of the human body. The fifth and the sixth electric flux lines interfere each other to generate a third low frequency active region for stimulating a specific part of the human body.

In view of the above, with the use of the characteristic of penetrating deeply into human bodies with two high-frequency currents interfere crisscrossingly along with the addition of a plurality of pieces of electrodes with electrical wires in a single interferential active region current stimulation system, a plurality of active regions can be generated. In addition, according to the body parts with electrodes attached thereto, various shapes and angles can be combined in order to conduct a plurality of interferential current stimulations therapy to a single organ with different angles or a plurality of organs.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 3A illustrates a schematic diagram of interferential current stimulation active regions for stimulating a joint portion.

FIG. 3B illustrates a front view of interferential current stimulation electrode positions and active regions thereof for stimulating a joint portion.

FIG. 3C illustrates a side view of interferential current stimulation electrode positions and active regions thereof for stimulating a joint portion.

DESCRIPTION OF EMBODIMENTS

Figure 1A:
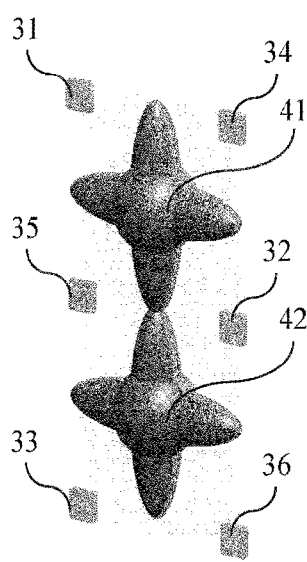
FIG. 1A illustrates a schematic diagram of interferential current stimulation active regions for stimulating a retus abdominis area and a back muscle area.

Reference will now be made in detail to the present preferred embodiments of the invention, examples of which are illustrated in the accompanying drawings. Wherever possible, the same reference numbers are used in the drawings and the description to refer to the same or like parts.

The method for interferential current stimulation by complex active regions of the present embodiment generates two low frequency active regions based on the configuration of six pieces of electrodes and corresponding electrical wires thereof, in which the arrangement position of the electrodes change along with the subject part or organs of the human body, such that the joint surface of the active regions may have an appropriate angle for attaching a specific site to be stimulated. Moreover, based on the interferential current stimulation method using six pieces of electrodes, a third low frequency active region can be formed by adding two additional electrodes, therefore, the variety of applications for the interferential current stimulation method on each part of the body in the present embodiment can be achieved with advantageous effects as describe in detail below.

Figure 1B:
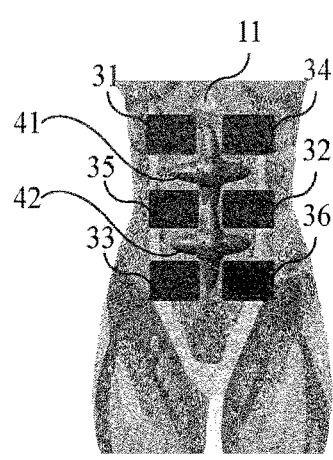
FIG. 1B illustrates a schematic diagram of interferential current stimulation electrode positions and active regions thereof for stimulating a retus abdominis area.
Figure 1C:
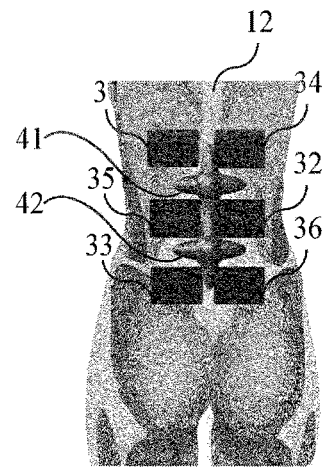
FIG. 1C illustrates a schematic diagram of interferential current stimulation electrode positions and active regions thereof for stimulating a back muscle area.
Figure 1D:
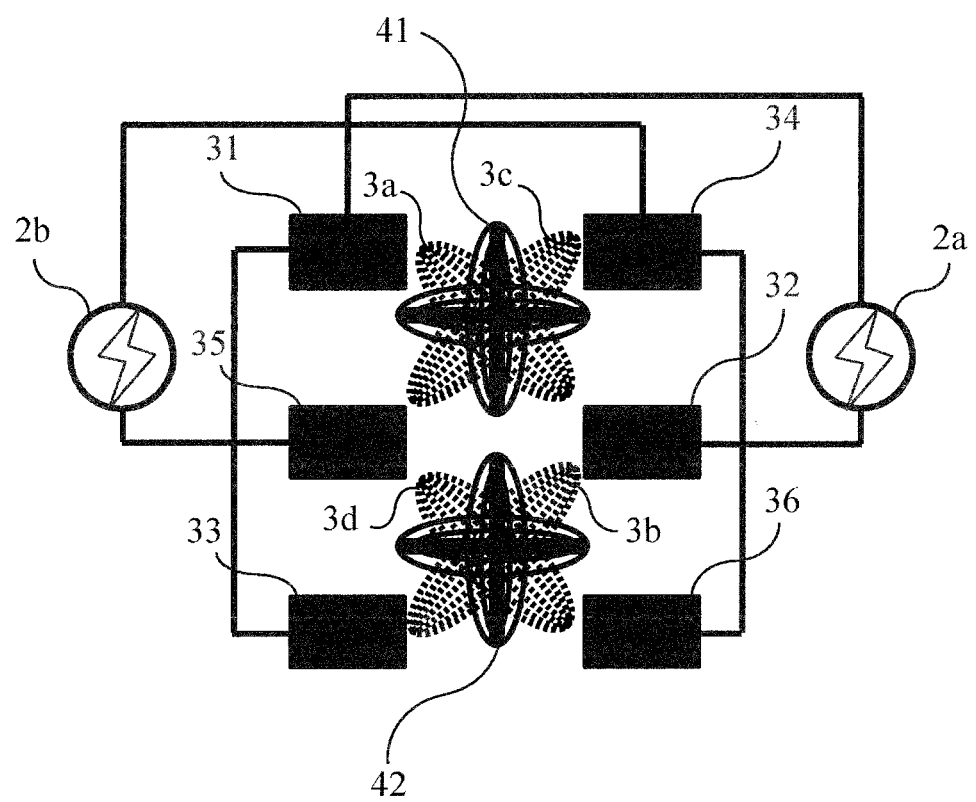
FIG. 1D illustrates an electrode power supply wiring diagram for the retus abdominis area and the back muscle area.

As shown in FIGS. 1A, 1B, 1C and 1D, FIG. 1A illustrates a schematic diagram of interferential current stimulation active regions for stimulating a Fetus abdominis area and a back muscle area. Since the shape of the retus abdominis area 11 and the back muscle area 12 are slender, only a single low frequency active region cannot fully cover these areas. The present method utilizes six pieces of electrodes to form two low frequency active regions for fully covering the retus abdominis area and the back muscle area. FIGS. 1B and 1C illustrate schematic diagrams of an interferential current stimulation method using six pieces of electrodes respectively applied to a retus abdominis area and a back muscle area. FIG. 1D illustrates an electrode power supply wiring diagram for the retus abdominis area and the back muscle area. Referring to FIG. 1D, both ends of the first frequency power source 2a are electrically connected, via the corresponding electrical wires, to the first electrode 31 and the second electrode 32, respectively, in which the first electrode 31 is further connected to the third electrode 33 so as to generate the first electric flux line 3a and the second electric flux line 3b. In addition, both ends of the second frequency power source 2b are electrically connected, via the corresponding electrical wires, to the fourth electrode 34 and the fifth electrode 35, respectively, in which the fourth electrode 34 is further connected to the sixth electrode 36 so as to generate the third electric flux line 3c and the fourth electric flux line 3d. The first electric flux line 3a and the third electric flux line 3c interfere each other for generating a first low frequency active region 41. Also, the second electric flux line 3b and the fourth electric flux line 3d interfere each other for generating a second low frequency active region 42. The first low frequency active region 41 and the second low frequency active region 42 are vertically arranged when attaching the human body so as to stimulate the retus abdominis area 11 or the back muscle area 12 of the human body 1.

In addition to stimulate the retus abdominis area 11 and the back muscle area 12, the core muscle also includes levator ani muscles 13, in which the levator ani muscles 13 have significant functions in the movements, postures and shaping of the human body. In particularly, for office workers who sit in offices all day without exercising and with poor postures, such muscles are likely to develop hack pains and obesity. Core muscle trainings are able to improve postures and eliminate the back pains.

Figure 2A:
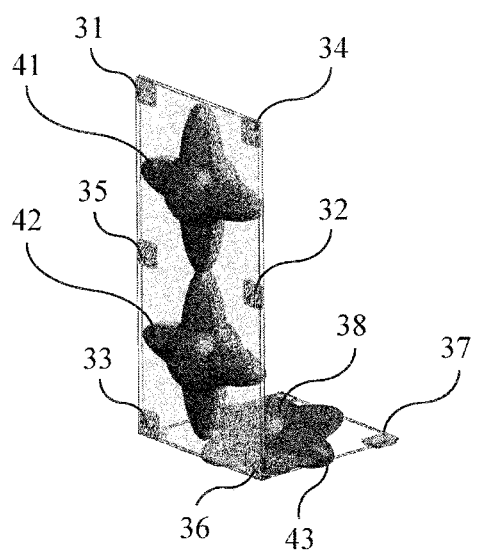
FIG. 2A illustrates a schematic diagram of interferential current stimulation active regions for stimulating a retus abdominis area and levator ani muscles.
Figure 2B:
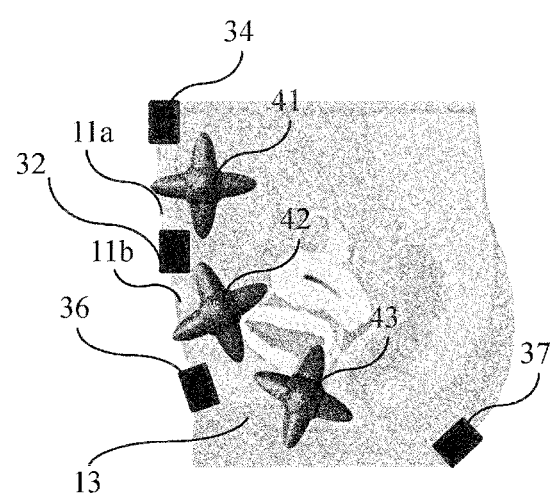
FIG. 2B illustrates a side view of interferential current stimulation electrode positions and active regions thereof for stimulating a retus abdominis area and levator ani muscles.
Figure 2C:
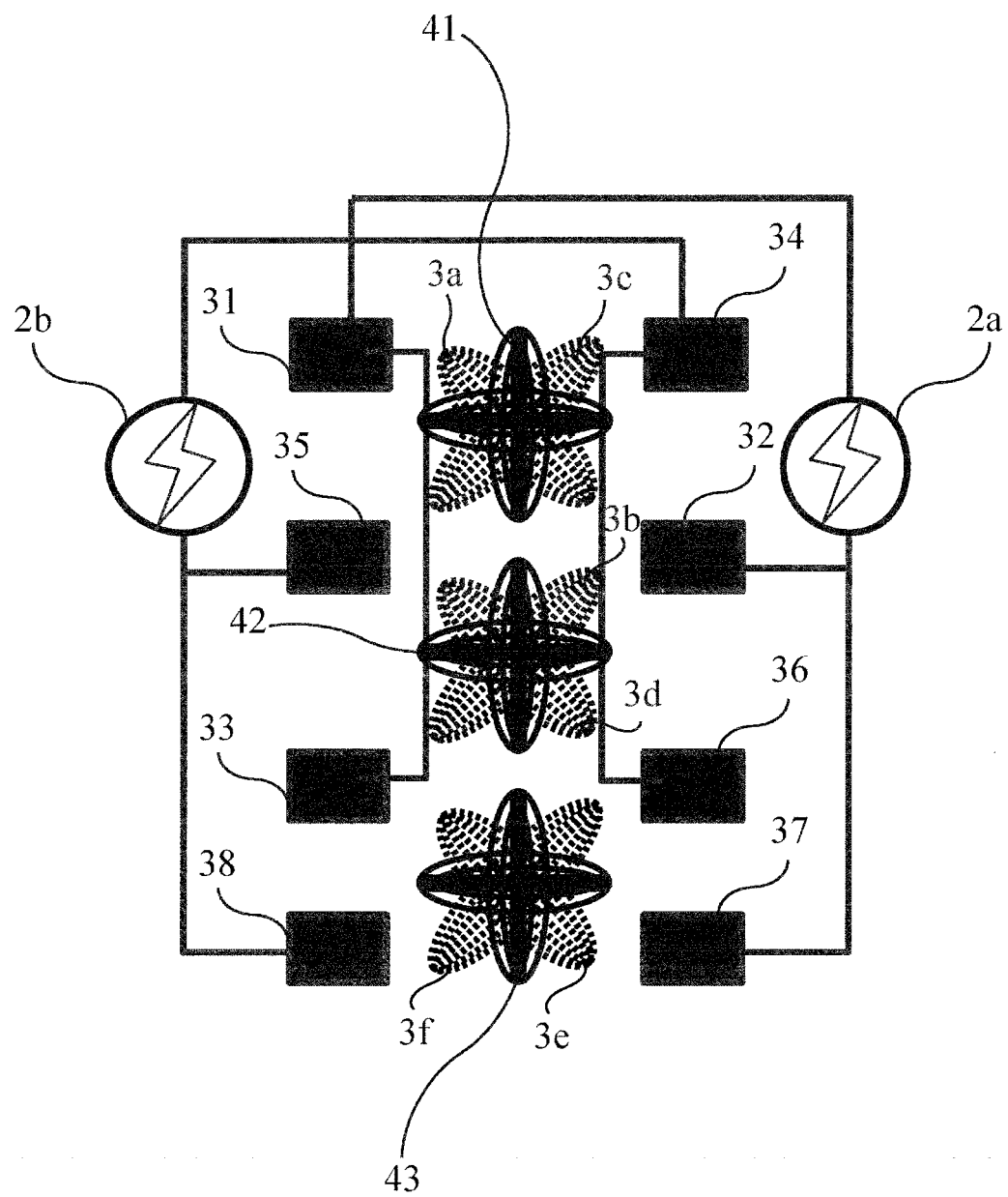
FIG. 2C illustrates an electrode power supply wiring diagram for a retus abdominis area and levator ani muscles.

As shown in FIGS. 2A, 2B and 2C, based on the electrodes configuration for stimulating the retus abdominis area 11 and the back muscle area 12, the present embodiment further provides the seventh electrode 37 and the eighth electrode 38 for interfering the original electrodes to generate the third low frequency active region 43 and stimulate the levator ani muscles 13 of the human body 1. FIG. 2A illustrates a schematic diagram of current stimulation active regions for stimulating a retus abdominis area and levator ani muscles. FIG. 2B illustrates a side view of interferential current stimulation electrode positions and active regions thereof for stimulating a retus abdominis area and levator ani muscles. FIG. 2C illustrates an electrode power supply wiring diagram for a retus abdominis area and levator ani muscles. In the present embodiment, the seventh electrode 37 and the eighth electrode 38 are respectively powered by the first frequency power source 2a and the second frequency power source 2b via the corresponding electrical wires; and the seventh electrode 37 and the eighth electrode 38 are respectively disposed on both sides beneath a hip area of the human body 1. The fifth electric flux line 3e is formed by the seventh electrode 37 and the third electrode 33, and the sixth electric flux line 3f is formed by the eighth electrode 38 and the sixth electrode 36. The fifth electric flux line 3e and the sixth electric flux line 3f interfere each other for generating a third low frequency active region 43 provided for stimulating the levator ani muscles 33 of the human body 1.

The interferential current stimulation method of the present embodiment can also be applied to joint portion 14 of the human body. Common degenerative joint diseases include the symptoms of pains and swelling. In general, the painful points of the joint portion 14 are the painful points around the front knee cap. Most swellings often occur at the arteries and lymph within the joint portions, and these portions are at the medial joint 14b. Therefore, low frequency active region is required to cover the portions of the lateral joint 14a and the medial joint 14b.

As shown in FIGS. 3A, 3B and 3C, FIG. 3A illustrates a schematic diagram of interferential current stimulation active regions for stimulating a joint portion, and FIGS. 3B and 3C respectively illustrate a front view and a side view of interferential current stimulation electrode positions and active regions covered perpendicular to the interferential current stimulation for joint portions.

Figures 3D, 3E, 3F:
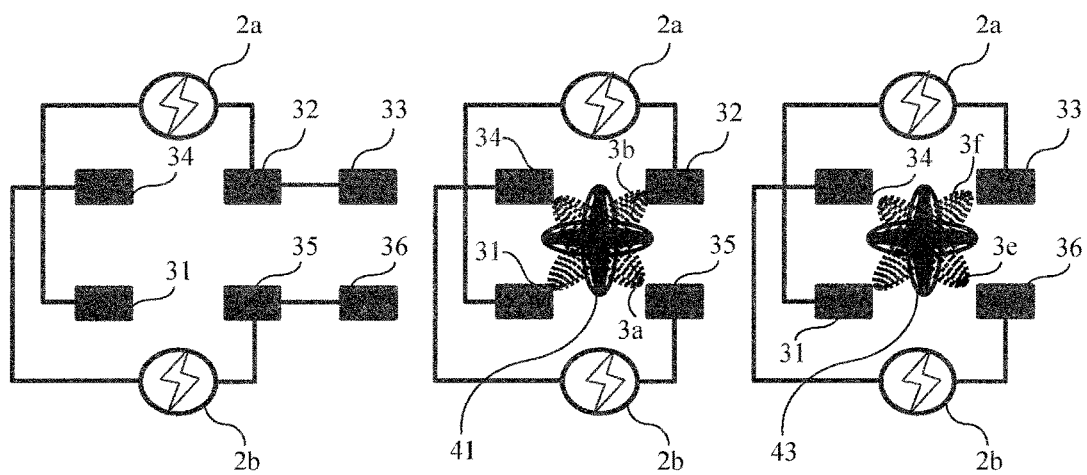
FIG. 3D illustrates an interferential current stimulation power supply wiring diagram for stimulating a joint portion.
FIG. 3E illustrates an interferential current stimulation power supply wiring diagram for stimulating specific positions on a lateral joint.
FIG. 3F illustrates an interferential current stimulation power supply wiring diagram for stimulating specific positions on medial joint.

As shown in FIGS. 3D, 3E and 3F, FIG. 3D illustrates an interferential current stimulation power supply wiring diagram for stimulating a joint portion, FIG. 3E illustrates an interferential current stimulation power supply wiring diagram for stimulating specific positions on a lateral joint, and FIG. 3F illustrates an interferential current stimulation power supply wiring diagram for stimulating specific positions on medial joint, in which the first electrode 31, the second electrode 32, the fourth electrode 34, and the fifth electrode 35 are respectively disposed on a plurality specific positions within a lateral joint 14a area of the human body 1, and the third electrode 33 and the sixth electrode 36 are respectively disposed on a plurality specific positions within a medial joint 14b area of the human body 1. The fifth electric flux line 3e is formed by the third electrode 33 and the first electrode 31, and the sixth electric flux line 3f is formed by the sixth electrode 36 and the fourth electrode 34. The fifth electric flux line 3e and the sixth electric flux line 3f interfere each other for generating a third low frequency active region 43 provided for stimulating lymph and blood at the joint portion 14 of the human body, in which the joint portion 14 includes knees, shoulders, wrists and ankles, etc.

In addition, women at work nowadays are often lack of exercises, leading to weaknesses in the lower abdomen 11b and the levator ani muscles 13, discomfort in excretion and urination as well as unfit body shapes. Furthermore, malposition and dystocia during pregnancy often occur in women with weak levator ani muscles. Therefore, since the interferential current stimulation active regions of the present embodiment can stimulate the lower abdomen 11b and the levator ani muscles 13, the effects of shrinking the lower abdomen 11b and to strengthen levator ani muscles 13 can be achieved. Also, the effects of weight-loss and beautifying figure can be achieved.

Figure 4A:
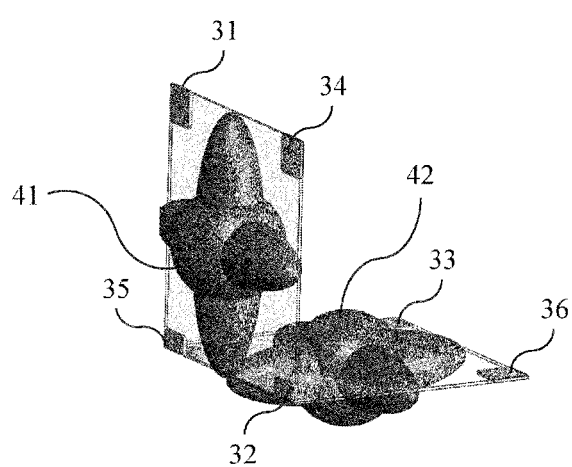
FIG. 4A illustrates a schematic diagram of interferential current stimulation active regions for stimulating lower abdomen and levator ani muscles.
Figure 4B:
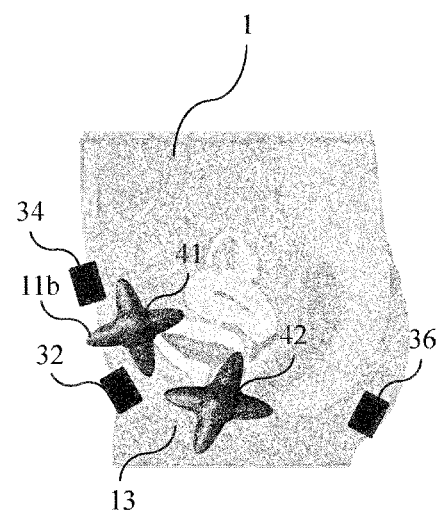
FIG. 4B illustrates a side view of interferential current stimulation electrode positions and active regions thereof for stimulating lower abdomen and levator ani muscles.
Figure 4C:
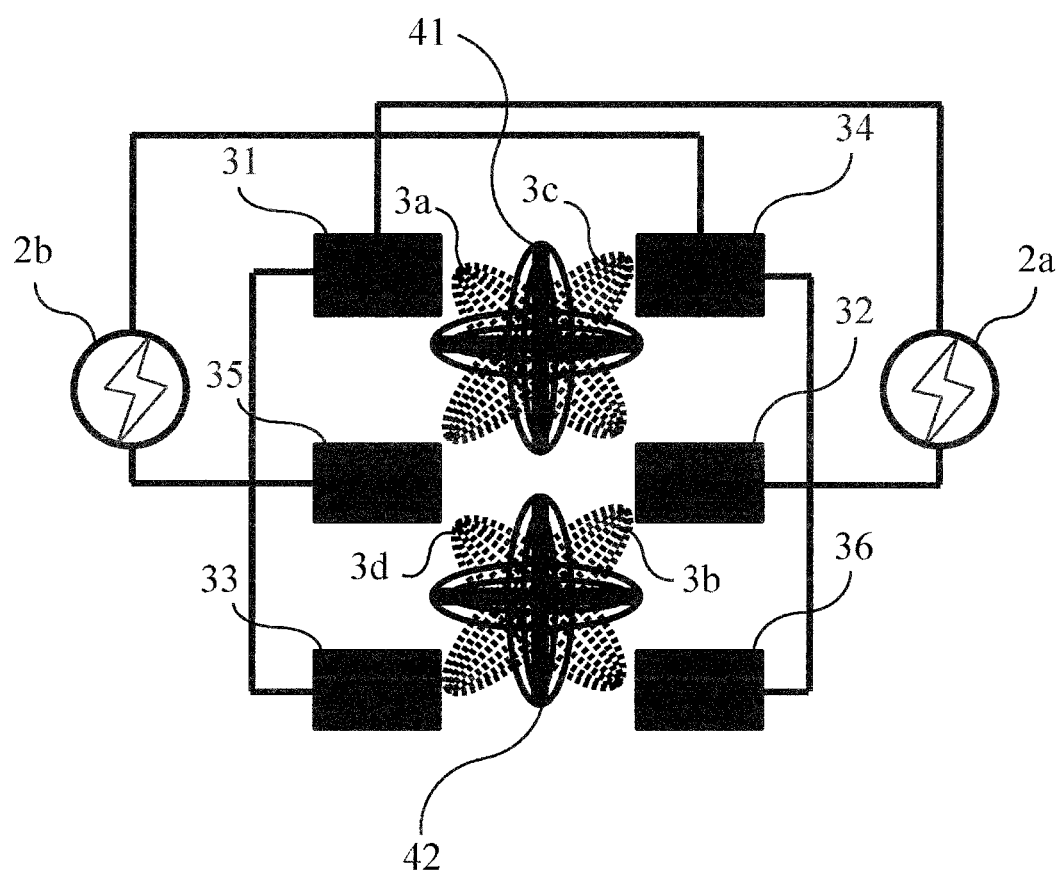
FIG. 4C illustrates an electrode power supply wiring diagram for lower abdomen and levator ani muscles.

As shown in FIGS. 4A, 4B and 4C, FIG. 4A illustrates a schematic diagram of interferential current stimulation active regions for stimulating lower abdomen and levator ani muscles, FIG. 4B illustrates a side view of interferential current stimulation electrode positions and active regions thereof for stimulating lower abdomen and levator ani muscles, and FIG. 4C illustrates an electrode power supply wiring diagram for lower abdomen and levator ani muscles. The first electrode 31, the second electrode 32, the fourth electrode 34, and the fifth electrode 35 are respectively disposed on a plurality of specific positions within a periphery area of the lower abdomen 11b of the human body 1, so that the periphery area of the lower abdomen 11b can be stimulated by the first low frequency active region 41. In addition, the third electrode 33 and the sixth electrode 36 are respectively disposed on both sides beneath the hip area of the human body 1 for stimulating the levator ani muscles 13 of the human body 1.

A Common rehabilitation method for postpartum recovering is to assist the contraction movement of the uterus 15 in order to enhance the metabolism and to eliminate unnecessary hormones as well as to repair damages from giving birth. By strengthening the levator ani muscles 13, urinary incontinences and the falling of uterus 15 can be prevented. Moreover, it is also important to shrink the lower abdomen 13 in body shaping and to improve waist pains. Consequently, the lower abdomen 11b, uterus 15 and the levator ani muscles 13 all need to be treated with interferential current stimulations at the same time.

Figure 5A:
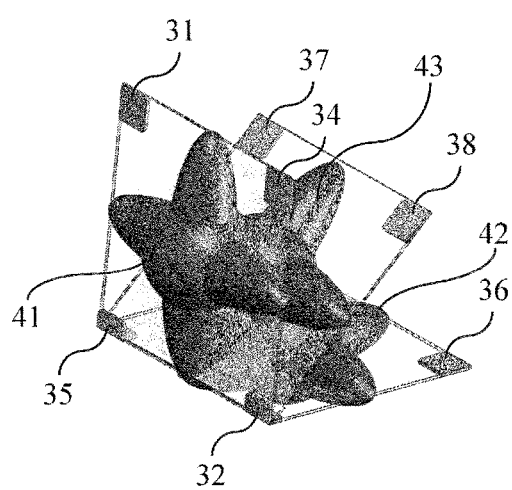
FIG. 5A illustrates a schematic diagram of interferential current stimulation active regions for stimulating lower abdomen, uterus and levator ani muscles.
Figure 5B:
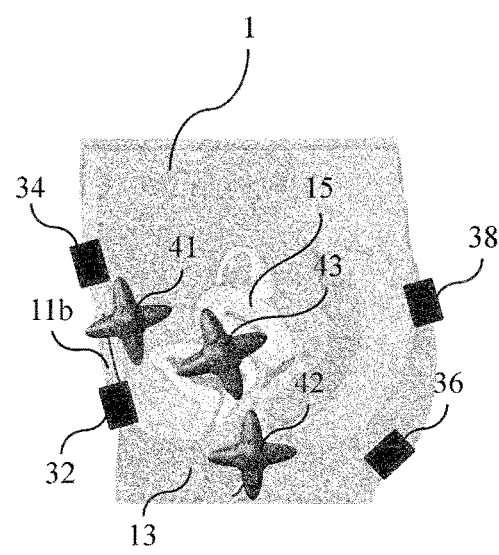
FIG. 5B illustrates a side view of interferential current stimulation electrode positions and active regions thereof for stimulating lower abdomen, uterus and levator ani muscles.
Figure 5C:
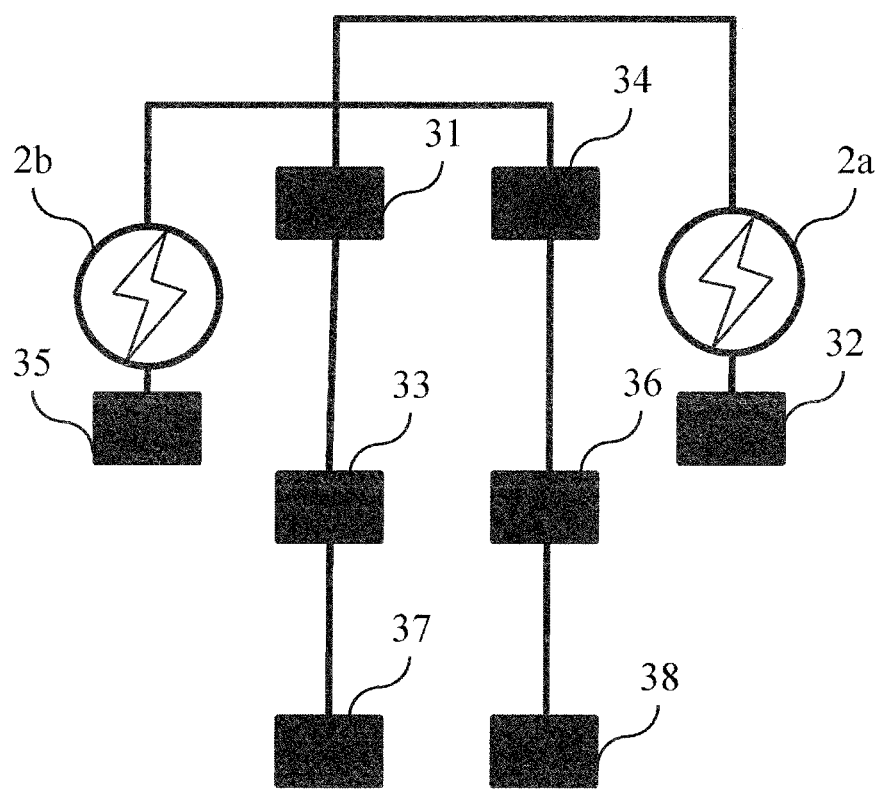
FIG. 5C illustrates an electrode power supply wiring diagram for lower abdomen, uterus and levator ani muscles.
Figures 5D, 5E, 5F:
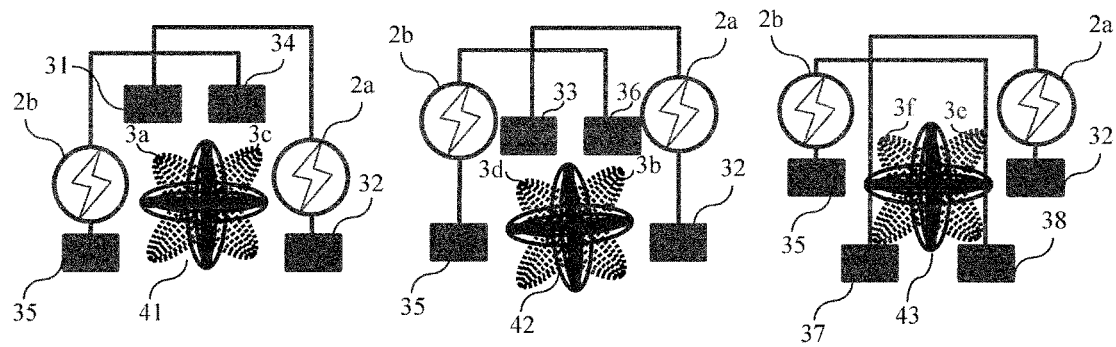
FIG. 5D illustrates an electrode power supply wiring diagram for lower abdomen.
FIG. 5E illustrates an electrode power supply wiring diagram for levator ani muscles.
FIG. 5F illustrates an electrode power supply wiring diagram for uterus.

As shown in FIGS. 5A, 5B, 5C, 5D, 5E and 5F, based on the electrodes configuration for stimulating the lower abdomen 11b and the levator ani muscles 13, the present embodiment further provides the seventh electrode 37 and eighth electrode 38 in order to form a third low frequency active region 43 for stimulating uterus 15. FIG. 5A illustrates a schematic diagram of interferential current stimulation active regions for stimulating lower abdomen, uterus and levator ani muscles. FIG. 5B illustrates a side view of interferential current stimulation electrode positions and active regions thereof for stimulating lower abdomen, uterus and levator ani muscles. FIG. 5C illustrates an electrode power supply wiring diagram for lower abdomen, uterus and levator ani muscles. FIG. 5D illustrates an electrode power supply wiring diagram for lower abdomen. FIG. 5E illustrates an electrode power supply wiring diagram for levator ani muscles. FIG. 5F illustrates an electrode power supply wiring diagram for uterus. The seventh electrode 37 and the eighth electrode 38 are respectively powered by the first frequency power source 2a and the second frequency power source 2b via the corresponding electrical wires. The seventh electrode 37 and the eighth electrode 38 are respectively disposed on both sides at a sacrum and coccyx area of the human body 1. A fifth electric flux line 3e is formed by the seventh electrode 37 and the second electrode 32, and a sixth electric flux line 3f is formed by the eighth electrode 38 and the fifth electrode 35. The fifth electric flux line 3e and the sixth electric flux line 3f interfere each other for generating a third low frequency active region 43 provided for stimulating the uterus area 15 of the human body 1.

According to medical researches, approximately half of all postnatal women have dysmenorrhea. Dysmenorrhea would generate pain not only at the abdomen 11a but also waist area. The interferential current stimulation method is able to relieve pains, activate cells around uterus 15 and enhance metabolisms of lymph as well as blood and eliminate prostaglandin or other unnecessary hormones associated with the pain.

Figure 6A:
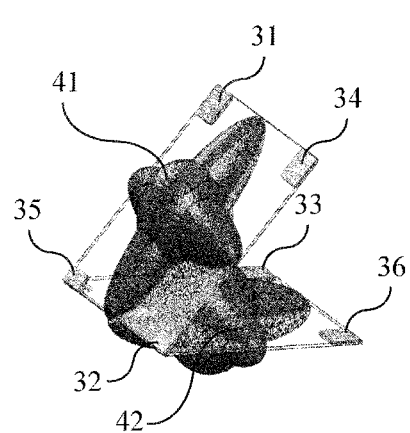
FIG. 6A illustrates a schematic diagram of interferential current stimulation active regions for stimulating uterus and levator ani muscles.
Figure 6B:
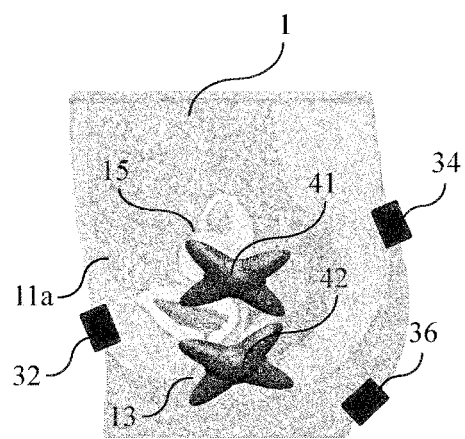
FIG. 6B illustrates a side view of interferential current stimulation electrode positions and active regions thereof for stimulating uterus and levator ani muscles.
Figure 6C:
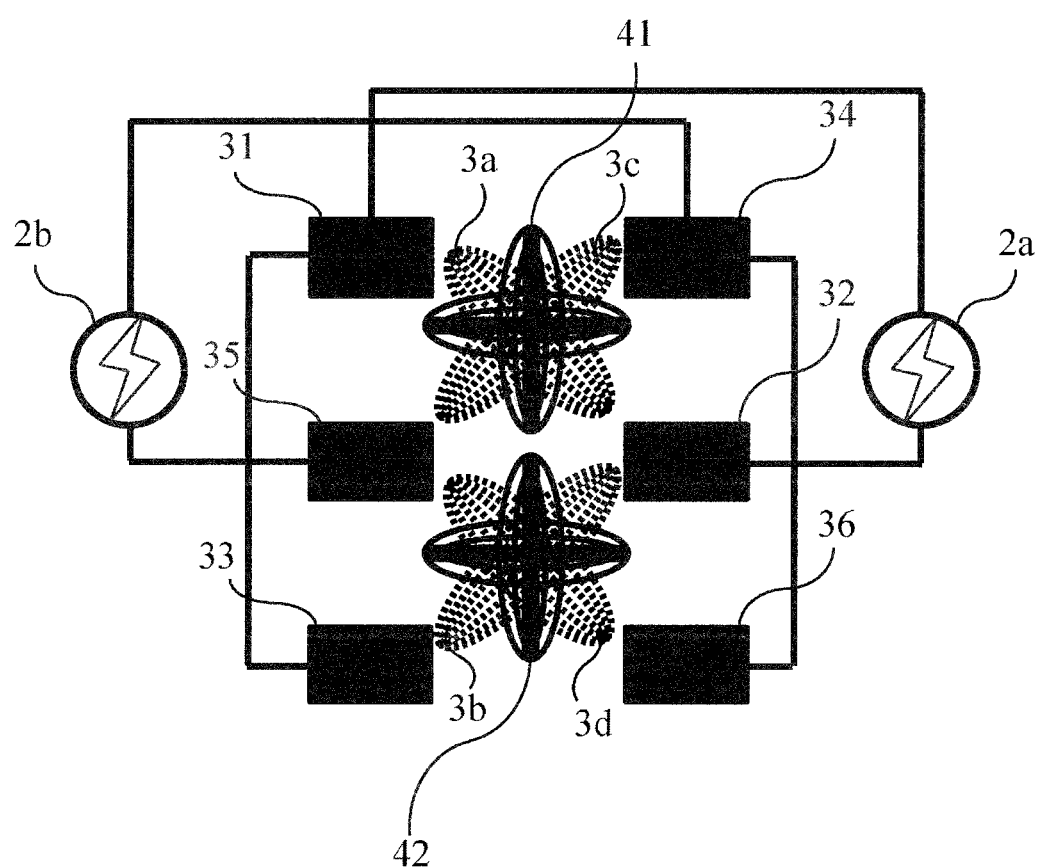
FIG. 6C illustrates an electrode power supply wiring diagram for uterus and levator ani muscles.

As shown in FIGS. 6A, 6B and 6C, FIG. 6A illustrates a schematic diagram of interferential current stimulation active regions for stimulating uterus and levator ani muscles, FIG. 6B illustrates a side view of interferential current stimulation electrode positions and active regions thereof for stimulating uterus and levator ani muscles, and FIG. 6C illustrates an electrode power supply wiring diagram for uterus and levator ani muscles. The second electrode 32 and the fifth electrode 35 are respectively disposed on both sides at lower abdomen 11 of the human body 1 and the first electrode 31 and the fourth electrode 34 are respectively disposed on both side at a sacrum and coccyx area of the human body 1, so that the uterus area 15 of the human body can be stimulated by the first low frequency active region 41. The third electrode 33 and the sixth electrode 36 are respectively disposed on both sides beneath the hip area of the human body 1, so that levator ani muscles 13 of the human body 1 can be stimulated by the second low frequency active region 42.

Moreover, the pelvic dysfunctions refer to injuries or weakness of pelvic floor muscles and urinary, excretory malfunctions, falling of uterus 15, incontinences, or even sexual disorders caused by the disorders of pudendal nerves of coccyx area. Typically, various types of interferential current stimulations needs to be applied to the uterus 15, the levator ani muscles 13 and the pudendal nerves of coccyx area 16 in order to improve the muscles at these areas of the body.

Figure 7A:
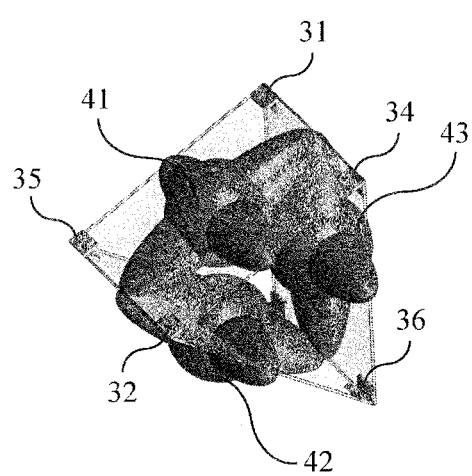
FIG. 7A illustrates a schematic diagram of interferential current stimulation active regions for stimulating uterus, levator ani muscles and pudendal nerves of sacrum and coccyx.
Figure 7B:
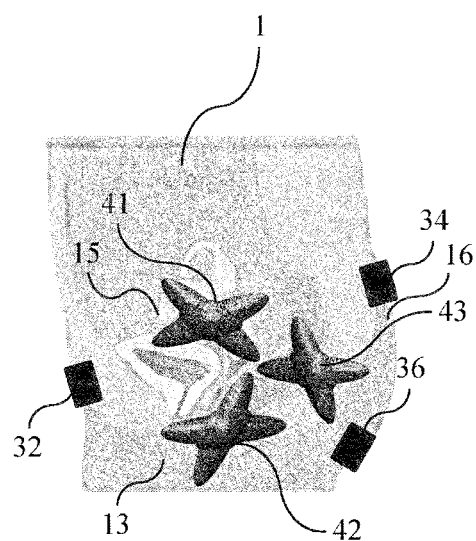
FIG. 7B illustrates a side view of interferential current stimulation electrode positions and active regions thereof for stimulating uterus, levator ani muscles and pudendal nerves of the sacrum and coccyx.
Figure 7C:
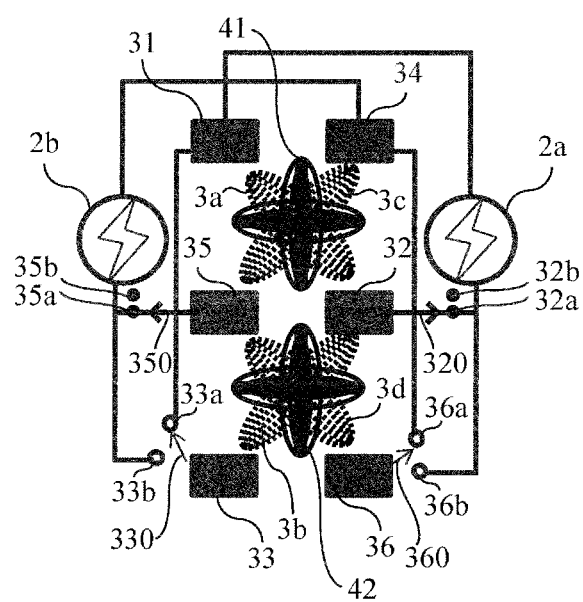
FIG. 7C illustrates a power switching schematic diagram of electrodes for stimulating uterus and levator ani muscles.
Figure 7D:
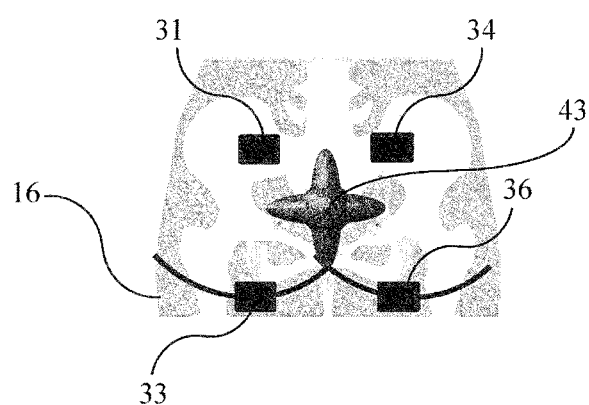
FIG. 7D illustrates a perspective view of interferential current stimulation electrode positions and active regions thereof for stimulating pudendal nerves of sacrum and coccyx.
Figure 7E:
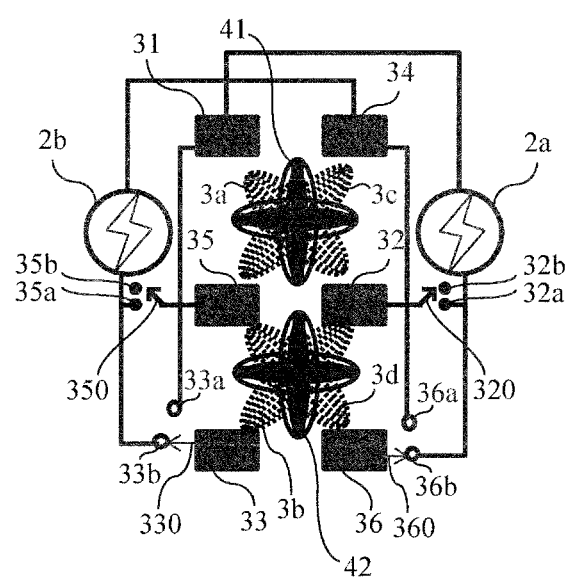
FIG. 7E illustrates a power switching schematic diagram of electrodes for stimulating uterus and pudendal nerves of sacrum and coccyx.
Figure 7F:
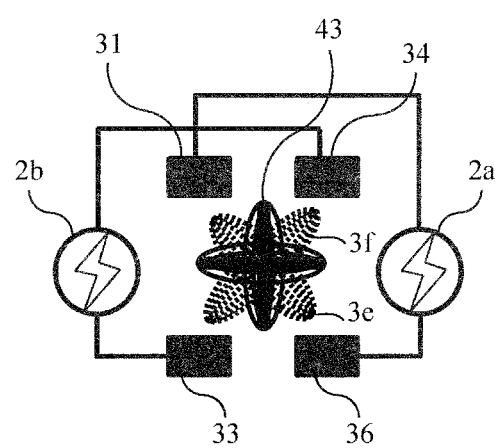
FIG. 7F illustrates corresponding electrodes and active regions thereof of uterus.

As shown in FIGS. 7A, 7B, 7C, 7D, 7E and 7F, based on the electrodes configuration for stimulating the uterus 15 and the levator ani muscles 13, the present embodiment further provides a first switching switch 330 and a second switching switch 360, configured to switch the power sources having different frequencies for the third electrode 33 and the sixth electrode 36, in which the electric flux line established between the third electrode 33 and the fourth electrode and the electric flux line established between the sixth electrode 36 and the first electrode 31 interfere each other, so as to form a third low frequency active region 43 for stimulating pudendal nerves 16 of the sacrum and coccyx. FIG. 7A illustrates a schematic diagram of interferential current stimulation active regions for stimulating uterus, levator ani muscles and pudendal nerves of sacrum and coccyx. FIG. 7B illustrates a side view of interferential current stimulation electrode positions and active regions thereof for stimulating uterus, levator ani muscles and pudendal nerves of the sacrum and coccyx. FIG. 7C illustrates a power switching schematic diagram of electrodes for stimulating uterus and levator ani muscles. FIG. 7D illustrates a perspective view of current stimulation electrode positions and active regions thereof for stimulating pudendal nerves of sacrum and coccyx. FIG. 7E illustrates a power switching schematic diagram of electrodes for stimulating uterus and pudendal nerves of sacrum and coccyx. FIG. 7F illustrates corresponding electrodes and active regions thereof of uterus. The third electrode 33 further includes a first switching switch 330 and corresponding electrical wires, and the third electrode 33 is switched to be powered by the second frequency power source 2b when the first switching switch is switched from the first switching circuit 33a to the second switching circuit 33b. The sixth electrode 36 further includes a second switching switch and corresponding electrical wires, and the sixth electrode 36 is switched to be powered by the first frequency power source 2a when the second switching switch is switched from the third switching circuit 36a to the fourth switching circuit 36h. In addition, the second electrode 32 further includes a first cut-off switch 320 and corresponding electrical wires, and the first frequency power source 2a stops to supply power to the second electrode 32 when the first cut-off switch 320 is switched from a first switching position 32a to a second switching position 32b. The fifth electrode 35 further includes a second cut-off switch 350 and corresponding electrical wires, and the second frequency power source 2b stops to supply power to the fifth electrode 35 when the second cut-off switch 350 is switched from the third switching position 35a to the fourth switching position 35b. The cut-off switches of the second electrode 32 and the fifth electrode 35 are turned-on when the switching switches of the third electrode 33 and the sixth electrode 36 are turned-on, so that a fifth electric flux line 3e is formed by the sixth electrode 36 and the first electrode 31 and a sixth electric flux line 3f is formed by the third electrode 33 and the fourth electrode 34. The fifth electric flux line 3e and the sixth electric flux line 3f interfere each other for generating a third low frequency active region 43 provided for stimulating pudendal nerves 16 of sacrum and coccyx.

To sum up, the objective of the present invention is to provide an interferential current stimulation system. In comparison to the known interferential current stimulation methods, the present invention requires the addition of only two to four electrodes configured in said interferential current stimulation system in order to form a plurality of low-frequency active regions. The key feature relies in the formation of specific shapes and angles at the joints of a plurality of active regions matching with different angles and sides of a single organ or a plurality of organs in order to widely cover organs acting on a plurality of interferential current stimulations as well as to achieve the effect of curing various symptoms and muscle trainings by attaching electrodes onto specific portions of the body. The above electrode fixing methods can be used on the specific positions of pelvic girdles, protective gears and flexible fabrics. An effective interferential current stimulation therapy is in progress correctly when these fixtures are put on.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A method for interferential current stimulation by complex active regions, adapted to generate a plurality of low frequency interference active regions formed of a plurality of staggered electric flux lines by disposing a plurality of electrodes so as to stimulate a plurality of specific parts of a human body by supplying electricity, comprising:

providing a power supply section configured to supply power having two different frequencies, wherein the power supply section comprises:
  a first frequency power source, comprising a current between 1,000 Hz and 10,000 Hz and corresponding electrical wires; and
  a second frequency power source, comprising a physiological frequency source between the region of decreasing or increasing less than 200 Hz of first frequency power source and corresponding electrical wires; and providing an electrode disposing section configured to provide a plurality of electrodes respectively connected to the first frequency power source and the second frequency power source via the corresponding electrical wires, wherein the electrode disposing section comprises:
  a first electrode electrically connected to the first frequency power source via a corresponding electrical wire and disposed on a specific position;
  a second electrode electrically connected to the second frequency power source via a corresponding electrical wire and disposed on a specific position that forming a first electric flux line with the first electrode;
  a third electrode electrically connected to the first frequency power source via a corresponding electrical wire and disposed on a specific position that forming a second electric flux line with the second electrode;
  a fourth electrode electrically connected to the second frequency power source via a corresponding electrical wire and disposed on a specific position;
  a fifth electrode electrically connected to the second frequency power source via a corresponding electrical wire and disposed on a specific position that forming a third electric flux line with the fourth electrode; and
  a sixth electrode electrically connected to the second frequency power source via a corresponding electrical wire and disposed on a specific position that forming a fourth electric flux line with the fifth electrode, wherein the first and the third electric flux lines interfere each other for generating a first low frequency active region provided for stimulating a specific part of the human body; and wherein the second and the fourth electric flux lines interfere each other for generating a second low frequency active region provided for stimulating another specific part of the human body.

2. The method for interferential current stimulation by complex active regions according to claim 1, wherein the first, the second, the third, the fourth, the fifth, and the sixth electrodes are respectively disposed on a plurality of specific positions within a retus abdominis area and an back muscle area of the human body, wherein the first and the second low frequency active regions are vertically arranged when attaching the human body so as to stimulate the retus abdominis area of the human body.

3. The method for interferential current stimulation by complex active regions according to claim 2, wherein the electrode disposing section further comprises a seventh electrode and an eighth electrode respectively powered by the first and the second frequency power sources via the corresponding electrical wires; wherein the seventh and the eighth electrodes are respectively disposed on both sides beneath a hip area of the human body, a fifth electric flux line is formed by the seventh electrode and the third electrode, and a sixth electric flux line is formed by the eighth electrode and the sixth electrode; and wherein the fifth and the sixth electric flux lines interfere each other for generating a third low frequency active region provided for stimulating levator ani muscles of the human body.

4. The method for interferential current stimulation by complex active regions according to claim 1, wherein the first, the second, the fourth, and the fifth electrodes are respectively disposed on a plurality specific positions within a lateral joint area of the human body, and the third and the sixth electrodes are respectively disposed on a plurality specific positions within a medial joint area of the human body; wherein a fifth electric flux line is formed by the third and the first electrodes, and a sixth electric flux line is formed by the sixth and the fourth electrodes; and wherein the fifth and the sixth electric flux lines interfere each other for generating a third low frequency active region provided for stimulating lymph and blood at a joint portion of the human body.

5. The method for interferential current stimulation by complex active regions according to claim 1, wherein the first, the second, the fourth, and the fifth electrodes of the electrode disposing section are respectively disposed on a plurality of specific positions within a periphery area of lower abdomen of the human body, so that the periphery area of the lower abdomen is stimulated by the first low frequency active region; and wherein the third and the sixth electrodes are respectively disposed on both sides beneath a hip area of the human body for stimulating levator ani muscles of the human body.

6. The method for interferential current stimulation by complex active regions according to claim 5, wherein the electrode disposing section further comprises a seventh electrode and a eighth electrode respectively powered by the first and the second frequency power sources via the corresponding electrical wires; wherein the seventh and the eighth electrodes are respectively disposed on both side at a sacrum and coccyx area of the human body, a fifth electric flux line is formed by the seventh electrode and the second electrode, and a sixth electric flux line is formed by the eighth electrode and the fifth electrode; and wherein the fifth and the sixth electric flux lines interfere each other for generating a third low frequency active region provided for stimulating an uterus area of the human body.

7. The method for interferential current stimulation by complex active regions according to claim 1, wherein the second and the fifth electrodes of the electrode disposing section are respectively disposed on both sides at lower abdomen of the human body and the first and the fourth electrodes are respectively disposed on both side at a sacrum and coccyx area of the human body, so that an uterus area of the human body is stimulated by the first low frequency active region; and wherein the third and the sixth electrodes are respectively disposed on both sides beneath a hip area of the human body, so that levator ani muscles of the human body is stimulated by the second low frequency active region.

8. The method for interferential current stimulation by complex active regions according to claim 7, wherein the third electrode further comprises a first switching switch and corresponding electrical wires, and the third electrode is switched to be powered by the second frequency power source when the first switching switch is turned-on; wherein the sixth electrode further comprises a second switching switch and corresponding electrical wires, and the sixth electrode is switched to be powered by the first frequency power source when the switching switch is turned-on; wherein the second electrode further comprises a first cut-off switch and corresponding electrical wires, and the first frequency power source stops to supply power to the second electrode when the first cut-off switch is switched from a first switching position to a second switching position; wherein the fifth electrode further comprises a second cut-off switch and corresponding electrical wires, and the second frequency power source stops to supply power to the fifth electrode when the second cut-off switch is switched from a third switching position to a fourth switching position; wherein the cut-off switches of the second and the fifth electrodes are turned-on when the switching switches of the third and the sixth electrodes are turned-on, so that a fifth electric flux line is formed by the sixth and the first electrodes and a sixth electric flux line is formed by the third and the fourth electrodes; and wherein the fifth and the sixth electric flux lines interfere each other for generating a third low frequency active region provided for stimulating pudendal nerves of sacrum and coccyx.

9. The method for interferential current stimulation by complex active regions according to claim 1, wherein, the electrode of the electrode disposing section of the interferential current stimulation by complex active regions and electrode wiring thereof can be fixed on a plurality of the specific positions of pelvic girdles, protective gears and flexible fabrics, providing an effective interferential current stimulation therapy correctly when these fixtures are put on.

10. The method for interferential current stimulation by complex active regions according to claim 2, wherein, the electrode of the electrode disposing section of the interferential current stimulation by complex active regions and electrode wiring thereof can be fixed on a plurality of the specific positions of pelvic girdles, protective gears and flexible fabrics, providing an effective interferential current stimulation therapy correctly when these fixtures are put on.

11. The method for interferential current stimulation by complex active regions according to claim 3, wherein, the electrode of the electrode disposing section of the interferential current stimulation by complex active regions and electrode wiring thereof can be fixed on a plurality of the specific positions of pelvic girdles, protective gears and flexible fabrics, providing an effective interferential current stimulation therapy correctly when these fixtures are put on.

12. The method for interferential current stimulation by complex active regions according to claim 4, wherein, the electrode of the electrode disposing section of the interferential current stimulation by complex active regions and electrode wiring thereof can be fixed on a plurality of the specific positions of pelvic girdles, protective gears and flexible fabrics, providing an effective interferential current stimulation therapy correctly when these fixtures are put on.

13. The method for interferential current stimulation by complex active regions according to claim 5, wherein, the electrode of the electrode disposing section of the interferential current stimulation by complex active regions and electrode wiring thereof can be fixed on a plurality of the specific positions of pelvic girdles, protective gears and flexible fabrics, providing an effective interferential current stimulation therapy correctly when these fixtures are put on.

14. The method for interferential current stimulation by complex active regions according to claim 6, wherein, the electrode of the electrode disposing section of the interferential current stimulation by complex active regions and electrode wiring thereof can be fixed on a plurality of the specific positions of pelvic girdles, protective gears and flexible fabrics, providing an effective interferential current stimulation therapy correctly when these fixtures are put on.

15. The method for interferential current stimulation by complex active regions according to claim 7, wherein, the electrode of the electrode disposing section of the interferential current stimulation by complex active regions and electrode wiring thereof can be fixed on a plurality of the specific positions of pelvic girdles, protective gears and flexible fabrics, providing an effective interferential current stimulation therapy correctly when these fixtures are put on.

16. The method for interferential current stimulation by complex active regions according to claim 8, wherein, the electrode of the electrode disposing section of the interferential current stimulation by complex active regions and electrode wiring thereof can be fixed on a plurality of the specific positions of pelvic girdles, protective gears and flexible fabrics, providing an effective interferential current stimulation therapy correctly when these fixtures are put on.

* * * * *